(12) United States Patent
Shah et al.

(10) Patent No.: US 10,064,970 B1
(45) Date of Patent: Sep. 4, 2018

(54) MULTIPLE FRAGRANCE EMISSION DEVICE

(71) Applicant: Trackmind Solutions LLC, New Brunswick, NJ (US)

(72) Inventors: Siddharth Shah, Freehold, NJ (US); Michael E. Bobev, Kendall Park, NJ (US); Srinivas R. Meda, Chester, NJ (US)

(73) Assignee: Trackmind Solutions LLC, New Bruswick, NJ (US)

( * ) Notice: Subject to any disclaimer, the term of this patent is extended or adjusted under 35 U.S.C. 154(b) by 53 days.

(21) Appl. No.: 15/282,730

(22) Filed: Sep. 30, 2016

Related U.S. Application Data

(60) Provisional application No. 62/236,558, filed on Oct. 2, 2015.

(51) Int. Cl.
  *B01F 3/04* (2006.01)
  *A61L 9/12* (2006.01)
  *A61L 9/03* (2006.01)

(52) U.S. Cl.
  CPC ............ *A61L 9/125* (2013.01); *A61L 9/122* (2013.01); *B01F 3/04085* (2013.01); *A61L 9/032* (2013.01); *A61L 9/035* (2013.01)

(58) Field of Classification Search
  CPC .............................. B01F 3/04; B01F 3/04085
  USPC ...................................... 261/30, 26, DIG. 88
  See application file for complete search history.

(56) References Cited

U.S. PATENT DOCUMENTS

| | | | |
|---|---|---|---|
| 5,167,877 A | * | 12/1992 | Pai .......................... A61L 9/122 261/18.1 |
| 6,548,025 B1 | | 4/2003 | Rasouli et al. |
| 6,802,460 B2 | | 10/2004 | Hess et al. |
| 7,734,159 B2 | | 6/2010 | Beland et al. |
| 7,783,380 B2 | | 8/2010 | York et al. |
| 8,385,730 B2 | | 2/2013 | Bushman et al. |
| 2010/0243754 A1 | | 9/2010 | Harris |
| 2013/0284821 A1 | | 10/2013 | Homer |

* cited by examiner

*Primary Examiner* — Robert A Hopkins
(74) *Attorney, Agent, or Firm* — Lerner, David, Littenberg, Krumholz & Mentlik, LLP

(57) ABSTRACT

A multi-fragrance emission device includes an insert having a top portion, a bottom portion, and at least one side portion, the insert including a passageway extending between an entrance at the top portion and an exit at the side portion. A fan is configured to move air through the passageway, and an outer shell is sized to fit over at least a portion of the insert. The outer shell includes a plurality of scent chambers, each scent chamber being in communication with one of a plurality of scent release holes. A motor is coupled to the insert, the motor configured to move the insert to align the exit of the insert with one of the plurality of scent release holes.

19 Claims, 6 Drawing Sheets

MULTIPLE FRAGRANCE EMISSION DEVICE

CROSS-REFERENCE TO RELATED APPLICATIONS

The present application claims the benefit of the filing date of U.S. Provisional Patent Application No. 62/236,558 filed Oct. 2, 2015, the disclosure of which is hereby incorporated herein by reference.

BACKGROUND

Fragrance emission devices for emitting pleasant fragrance in enclosed environments, for example, are known. Such devices may be used to mask odors in spaces such as restrooms and kitchens. However, many of the known fragrance emission devices are configured to receive a single reservoir of fragrance. Thus, if a user desires to change the type of fragrance, the fragrance reservoir needs to be replaced with the desired type and the removed fragrance type must then be stored carefully for future use or be prematurely disposed of.

SUMMARY

It may be cumbersome to maintain and store multiple partially used fragrance reservoirs. An embodiment permits a user to easily select a desired type of fragrance from an assortment of fragrances. More particularly, this includes a fragrance dispenser comprising a housing configured to removably receive a plurality of scent cartridges, each of the plurality of scent cartridges having an air inlet and an air outlet, a member movably associated with the housing, the member having a first opening, a fan configured to move air through the air inlet and the air outlet of the selected one of the plurality of scent cartridges, and a motor coupled to the member and configured to move the member relative to the housing. The member is configured to be moved about the housing to selectively align the first opening with at least one of the air inlet and the air outlet of at least a selected one of the plurality of the scent cartridges.

According to another embodiment, a fragrance emission device comprises a base including a plurality of ducts, each of the plurality of ducts extending from an end portion of the base to a side portion of the base, a plurality of inlet openings at the end portion of the base, each of the plurality of inlet openings being in communication with one of the plurality of ducts, a plurality of outlet openings at the side portion of the base, each of the plurality of outlet openings being in communication with one of the plurality of ducts, a fan positioned at the end portion of the base adjacent the plurality of inlet openings, a motor in communication with the fan and adapted to actuate the fan, a plurality of fragrance cartridges, each of the plurality of fragrance cartridges positionable to at least partially align with one of the plurality of outlet openings, and a cover adapted to fit over the base, the cover including a release opening, configured so as align the release opening with one of the plurality of outlet openings.

According to yet another embodiment, a system for emitting a variety of fragrances comprises a base including a passageway extending from an end portion of the base to a side portion of the base and having an inlet opening at the end portion, a plurality of outlet openings at the side portion of the base, each of the plurality of outlet openings being in communication with the passageway, a fan positioned at the end portion of the base adjacent the inlet opening, a motor in communication with the fan and adapted to actuate the fan, a plurality of fragrance cartridges, each of the plurality of fragrance cartridges positionable to at least partially align with the plurality of outlet openings, and a cover adapted to fit over the base, the cover including a release opening, and being rotatable with respect to the base, such that the release opening aligns with one of the plurality of outlet openings.

DETAILED DESCRIPTION

Figure 1A:
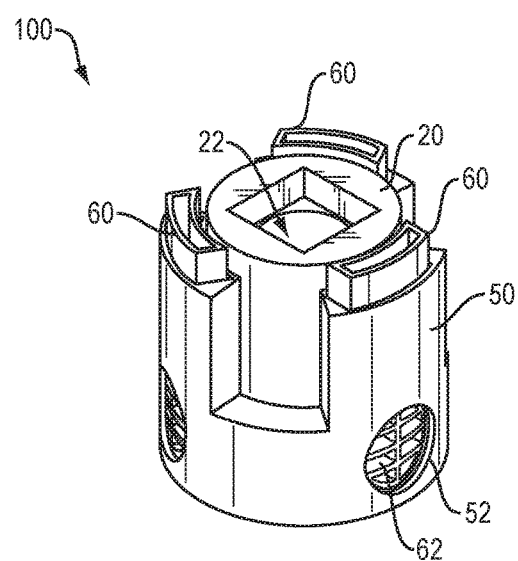
FIG. 1A is a perspective view of a multi-chamber scent diffuser according to an embodiment.
Figure 1B:
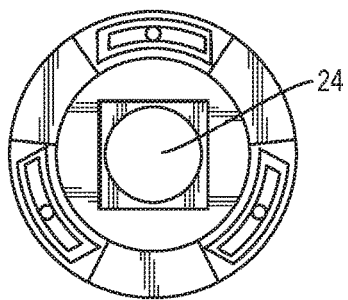
FIG. 1B is a top view of the multi-chamber scent diffuser of FIG. 1A.
Figure 1C:
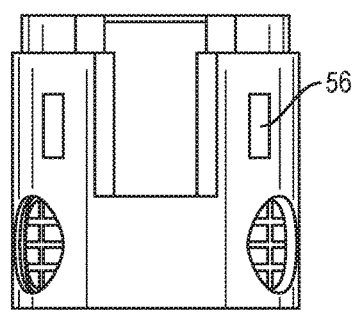
FIG. 1C is a side view of the multi-chamber scent diffuser of FIG. 1A.

FIGS. 1A-1C illustrate an example multi-scent diffuser 100. In this example, the diffuser includes an annular outer shell 50 enclosing an opening 59 (FIG. 4C), a plurality of scent cartridges 60, and an insert 20 having a passageway 22. The passageway 22 has an entrance 24 at a top portion of the insert 20, and an exit 28 (FIG. 2) at a side portion, as more fully described in connection with FIG. 2. The outer shell 50 has a plurality of scent release holes 52, each being in communication with a particular fragrance cartridge 60. Each fragrance cartridge 60 may be filled with a different fragrance. When the exit 28 of the insert 20 aligns with one of the scent release holes 52 in the outer shell 50, air flowing through the passageway 22 of the insert pushes scent from the scent cartridge 60 out of the scent release hole 52. The air may be forced through the passageway 22 using, for example, one or more fans 90 (FIG. 5). At least one of the insert 20 and the outer shell 50 may be rotated relative to one another, thereby varying the alignment of the exit hole 28 of the insert 20 and particular scent release holes 52. The rotation may be actuated by a motor 40 (FIG. 2C), which may be controlled by a microcontroller (not shown) or other computing device. In some examples, the microcontroller may be programmed to switch the alignment of the exit hole 28 between two or more scent release holes 52 at a predetermined frequency, thus essentially mixing the fragrances. In other examples, the microcontroller may be programmed to vary a speed of the fan 90, such that an intensity of the fragrance emitted increases and decreases.

Figure 2A:
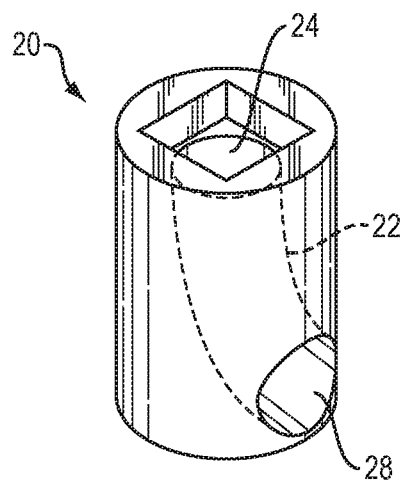
FIG. 2A is a perspective view of an insert of the diffuser of FIGS. 1A-1C.
Figure 2B:
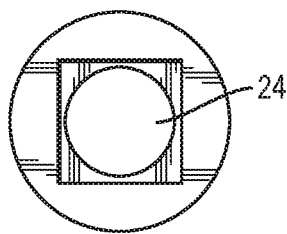
FIG. 2B is a top view of the diffuser.

FIGS. 2A-2B illustrate the insert 20. The passageway 22 of the insert 20 extends between entrance 24 and exit 28. In some examples, the passageway 22 may be a duct having a width approximately a same size as the entrance 24 and the exit 28. The duct may be curved or straight. In other examples, the passageway 22 may have a width greater than a size of the entrance 24 or exit 28. For example, the passageway 22 may extend nearly a full diameter of the insert 20. While the entrance 24 and exit 28 are shown as being circular, it should be understood that any shape may be used. Moreover, the size of the entrance 24 and exit 28 may be varied.

Figure 2C:
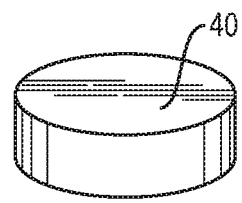
FIG. 2C is an example motor in communication with the insert of FIG. 1.

FIG. 2C illustrates an example motor assembly 40 adapted to adjust a positioning of the insert 20 relative to the outer shell 50. For example, the insert 20 may sit on top of the motor assembly 40, and the motor assembly 40 may cause the insert 20 to rotate such that a lateral orientation of the exit 28 relative to the outer shell 50 is varied.

The motor assembly 40 may in some examples include a computing device, such as a microcontroller, programmed to rotate the insert 20 or otherwise adjust its position. In other examples, the moor assembly 40 may include a device configured to communicate with a remote computing device, such that the motor may be actuated by commands sent by the remote computing device. Whether included in the motor assembly 40 or being remote, the computing device may include a memory storing information accessible by a processor, including instructions that may be executed by the processor. Memory also includes data that may be retrieved, manipulated or stored by the processor. The memory may be of any type capable of storing information accessible by the processor, such as a hard-drive, memory card, ROM, RAM, DVD, CD-ROM, write-capable, and read-only memories. The processor may be any well-known processor or a dedicated controller, such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. The instructions may be executed to actuate the motor assembly 40, thereby adjusting a positioning of the exit 28. The instructions may include commands to change a direction, speed, or frequency of the adjusting. In some examples, the motor assembly, or a second motor assembly also coupled to the computing device and similarly configured, may actuate a fan (FIG. 5) which pushes air through the hollow chamber of the insert 20.

Data may be retrieved, stored or modified by processor in accordance with the instructions. For instance, although the system and method is not limited by any particular data structure, the data may be stored in computer registers, in a relational database as a table having a plurality of different fields and records, or XML documents. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

According to one example, the computing device may be programmed to emit fragrances in a predefined pattern. The fragrance emission pattern may resemble a schedule for emitting selected fragrances, and may further include conditions for emitting selected fragrances. For example, the fragrance emission pattern may be one or more algorithms causing emission of one or more fragrances in response to detecting one or more environmental conditions, such as weather, time, location, etc.

Figure 3:
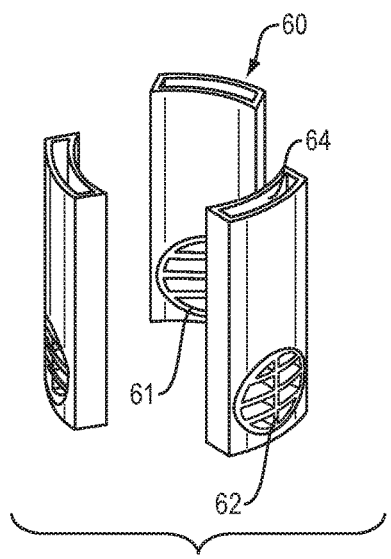
FIG. 3 is a perspective view of example scent cartridges of the diffuser of FIGS. 1A-1C.

FIG. 3 illustrates example fragrance cartridges 60. The cartridges 60 may include a reservoir 64, and have an air inlet 61 and an air outlet 62 at a lower portion of the reservoir. The air outlet 62 may be covered by, for example, a porous material. In this regard, liquid, such as perfumed oil, may fill the reservoir 40 and be slowly released through the air outlet 62. Each fragrance cartridge 60 may be filled with a different scent. In some examples, the cartridge may also include a wick.

While the fragrance cartridges 60 are shown as being generally rectangular, and curved corresponding to a shape of the outer shell, it should be understood that any shape is possible. For example, the cartridges may be discs or spheres or any other shape corresponding to a shape of the scent release holes 52 in the outer shell 50. Moreover, rather than being filled with liquid, the cartridges may be filled with any scented substance, such as wax, papers, etc. The cartridges 60 may be made from any material, such as stainless steel, plastic, wood, glass, etc.

According to one example, each fragrance cartridge may also include a contact point (not shown) that is complementary to a contact point of a heating element (not shown) arranged in the outer shell 50. In this example, when a particular fragrance cartridge is selected, the associated heating element may be activated, thereby warming the cartridge housing the selected fragrance. Such warming may facilitate release of the fragrance by the air flowing through the outlet 62 and scent release hole 52.

Figure 4A:
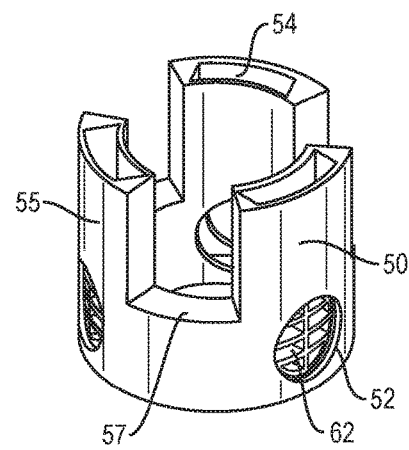
FIGS. 4A-4C are various views of an outer shell of the diffuser of FIGS. 1A-1C.
Figure 4B:
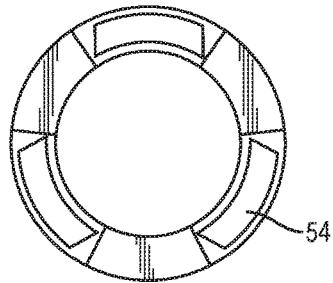
Figure 4C:
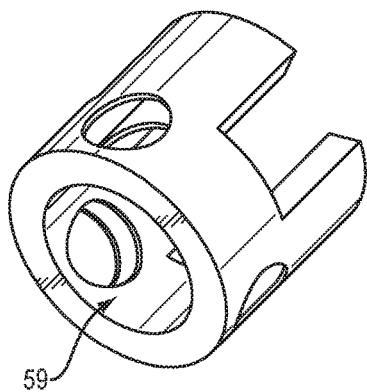
Figure 5:
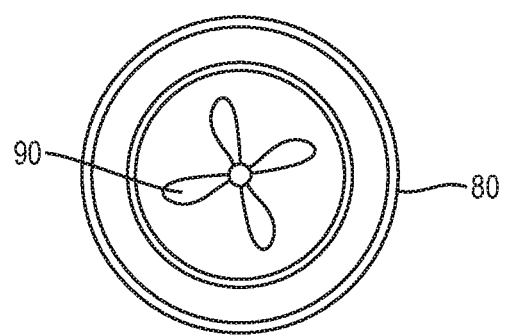
FIG. 5 is an example top view of a cover for the diffuser of FIGS. 1A-1C.

FIGS. 4A-4C illustrate details of the outer shell 50. The outer shell 50 includes a plurality of compartments 54 for receiving the plurality of fragrance cartridges 60. As shown, the compartments 54 are defined within raised portions 55 of the outer shell 50, wherein the raised portions 55 extend between recessed portions 57. However, it should be understood that in other examples the outer shell 50 may be all the same height. Moreover, while the outer shell 50 shown includes three compartments 54, it should be understood that any number of compartments may be included. Moreover, a size and shape of the compartment may be varied to accommodate different sized/shaped fragrance cartridges.

At a bottom portion of each compartment is a scent release hole 52. The hole 52 aligns with the outlet 62 of the fragrance cartridge 60. Depending on an orientation of the insert 20 (FIG. 2) within the outer shell 50, the exit 28 of the insert 20 will also align with one of the air inlet 61 of the fragrance cartridge and the corresponding scent release hole 52 of the outer shell 50. In this regard, air flowing through the passageway 22 of the insert 20 will pass through the air inlet 61 and the air outlet 62 of one of the fragrance cartridges 60 and further to the surrounding environment through the corresponding scent release hole 52.

As mentioned above, the outer shell 50 may include one or more heating elements (not shown). For example, a heating device may be positioned near a bottom portion of the outer shell 50, wherein the heating device includes contact points extending into each of the compartments 54. The heating device may selectively deliver energy through one of the contact points to provide heat to a selected fragrance cartridge 60 having a corresponding contact point coupled thereto.

As shown in FIG. 4C, the outer shell 50 encloses the opening 59. In this regard, the motor assembly 40 (FIG. 2C)

and the insert 20 may be accommodated within the opening 59 of the outer shell 50 and contact a resting surface, such as a table, shelf, floor, etc and serve as a base for the fragrance device 100.

The outer shell 50, or another portion of the device, may also include one or more status indicators schematically illustrated as elements 56 (FIG. 1C). For example, the status indicators 56 may include light emitting diodes, displays, or any other types of visual or audio indicator. The indicators 56 may identify, for example, which fragrance is being released and/or an intensity level of the released fragrance. Alternatively or additionally, the indicators may identify a level of fragrance remaining in each cartridge.

FIG. 5 illustrates an example cover 80 which may be placed over a top portion of the fragrance dispenser 100. For example, an outer perimeter of the cover 80 may be coextensive with an outer surface of outer shell 50 when the cover is in place. In other examples, the outer perimeter of the cover 80 may extend beyond the outer surface of the outer shell 50, or may alternatively only cover the insert 20.

The cover 80 may include a fan 90, configured to blow air through the passageway 22 of the insert 20. The fan may be actuated by the motor in the motor assembly 40 in conjunction with the computing device, or by a separate motor and computing device. The fan 90 may be situated above a top surface of the insert 20 when the cover 80 is in place. Alternatively, the fan 90 may be positioned partially or fully within the passageway. While one fan 90 is shown in FIG. 5, any number of fans may be included.

Figure 6:
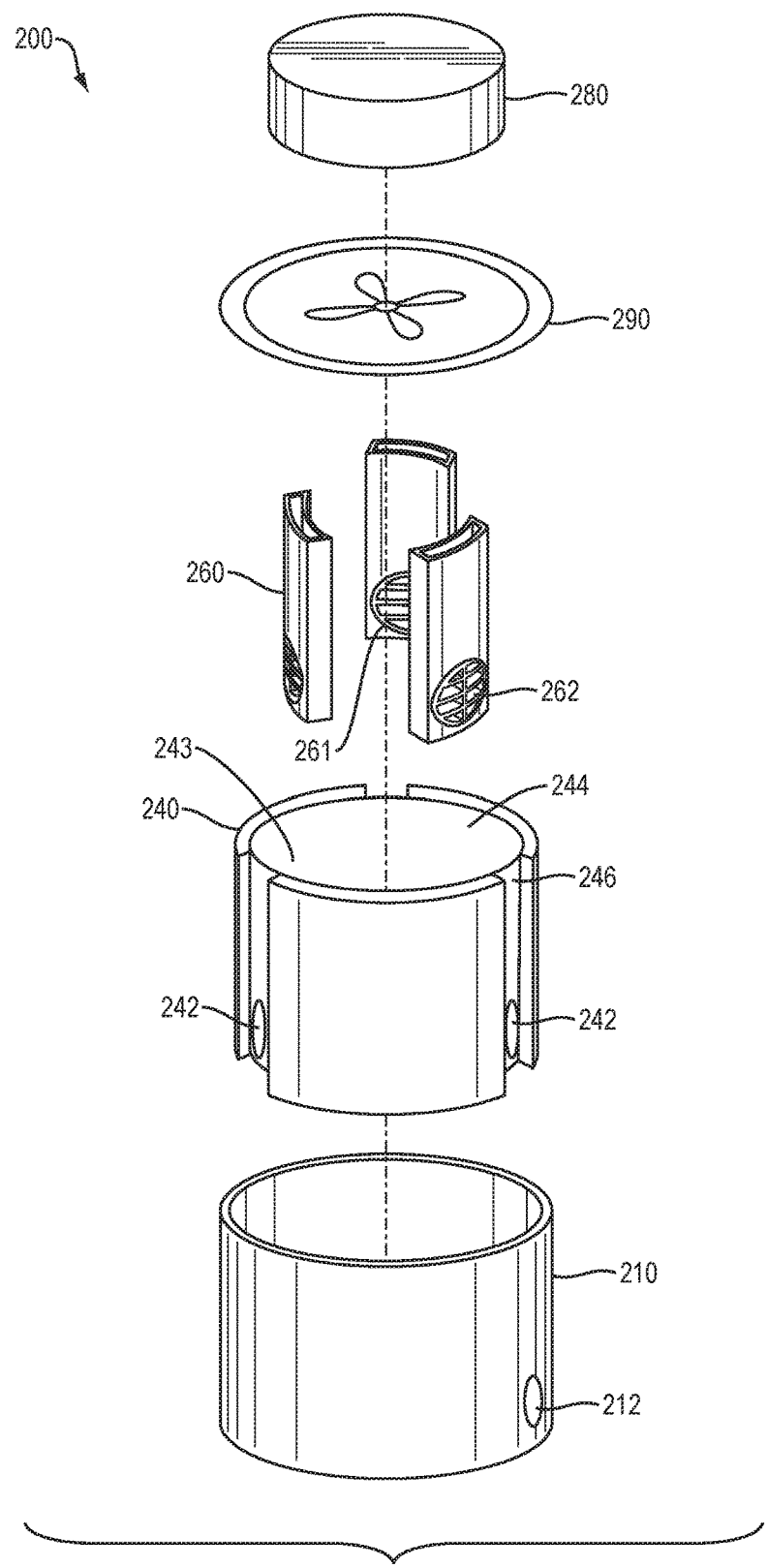
FIG. 6 is an exploded view of an example diffuser according to another embodiment.

FIG. 6 illustrates another example embodiment of a multi fragrance dispenser 200. A base 240 includes an air inlet 244, a plurality of outlet openings 242, and a passageway 243 extending between the air inlet and the plurality of outlet openings. The base 240 further includes a plurality of receptacles 246 adapted to receive fragrance cartridges 260. When the fragrance cartridges 260 are engaged with the base 240, a cartridge air inlet 261 of each cartridge 260 aligns with one of the outlet openings 242 in the base. Cover 210 is sized and shaped to fit over the base 240, and includes a release opening 212. At least one of the base 240 and the cover 212 is repositionable with respect to the other, such that the release opening 212 can align with a selected one of the outlet openings 242 in the base and the outlet 262 of the cartridge. As such, a fan 290, actuated by motor/control circuitry 280, pushes air through the passageway 243 through the inlet 244 of the base, and the air passes through outlet opening 242, the air inlet 261 and the cartridge outlet 262 of one of the cartridges 260 and that is aligned with the release opening 212, and into the surrounding environment.

The motor/control circuitry 280 may include any type of motor and small or remote computing device, as described in connection with previous embodiments.

The fan 290 may be positioned over the inlet 244 of the base 240. In some examples, the fan 290 may be positioned at least partially within the inlet 244. While one fan is shown, any number of fans may be used. For example, a plurality of smaller fans may be used.

The receptacles 246 may include tracks (not shown) corresponding to features (not shown) on the side and/or back surfaces of the fragrance cartridges 262 to retain the cartridges in position. In other examples, the cartridges may engage within the receptacles 246 by interference fit, adhesive, snap fit, or any other engaging technique. While the fragrance cartridges 260 are shown as being generally rectangular with a curve corresponding to the shape of the base 240, different configurations may be used. Moreover, the fragrance cartridges may include any type of fragrance retaining and releasing mechanism, such as a porous sheet in communication with a fluid-filled reservoir, a wick, fragrance beads, wax cubes, scented paper, etc.

While the base 240 and cover 210 are shown as being generally cylindrical, other shapes may be used. For example, the base 240 may be generally spherical. Alternatively, the base 240 and cover 210 may be rectangular. In this example, rather than rotating at least one of the base or the cover to vary the dispersed fragrance, a plurality of release openings 212 may be included in the cover 210 such that each release opening of the cover aligns with one outlet opening of the base. The release opening of the cover may each include a movable door or panel or other covering (not shown), such that the holes corresponding to fragrances not desired to emitted can be kept covered. Such a door or panel or covering may be movable by the motor and controller circuitry 280.

While the passageway 261 of the base 240 is illustrated as being delimited by the entire periphery of the base 240, in other examples the passageway 261 may include a plurality of ducts defined in the base 240 and associated with the outlet openings 242.

Figure 7:
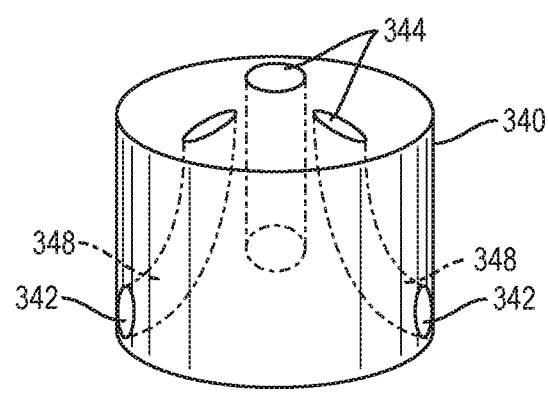
FIG. 7 is a perspective view of an example base according to another embodiment.

FIG. 7 illustrates an example base 340 having an alternative internal configuration. In this example, the base 340 includes a plurality of ducts 348. Each duct 348 extends between an inlet 344 at an upper portion of the base 340 and an outlet 342 at a lower side portion of the base 342. The ducts 348 are shown as being curved in a generally arcuate shape. In this example, a plurality of fans may be positioned over the base, such that each duct inlet 344 has a particular fan positioned over it. The fans may be selectively actuated, such that only one fan is actuated at a given time to move air through a duct associated with a selected fragrance. For the purpose of clarity, the receptacles for receiving the fragrance cartridges are not shown in FIG. 7.

Figure 8:
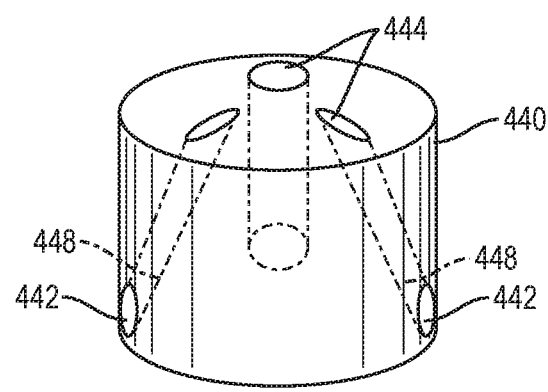
FIG. 8 is a perspective view of another example base according to another embodiment.

FIG. 8 illustrates another example base 440 having another internal configuration. Similar to the base 340, the base 440 includes a plurality of ducts 448 extending between inlets 444 at an upper portion of the base 440 and outlets 442 at a lower side portion of the base 440. However, the ducts 448 extend generally straight and at an angle with respect to a vertical axis of the base. For the purpose of clarity, the receptacles for receiving the fragrance cartridges are not shown in FIG. 8.

Although not shown, in some examples the multi-fragrance emission device may also include a power supply, such as a battery. The power supply may be used to power the controller circuitry, motor, etc.

The systems and methods described above enable a variety of fragrances to be released, without requiring a multitude of separate diffusers and without requiring a user to continually manually change the fragrance cartridges. Additionally, the device may be programmed to mix selected scents, for example, by oscillating back and forth between two or more scents. Moreover, the device can be programmed to release scent at an intensity and frequency that is desirable to a user, such as by slowly increasing an amount of the fragrance that is released. The device can be further programmed to release particular scents or patterns of scents at predetermined times.

As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.", "including" and the like) should not be interpreted as limiting the claimed subject matter to the specific examples; rather, the examples are intended to illustrate only some of many possible aspects.

The invention claimed is:

1. A fragrance dispenser, comprising:
a housing configured to removably receive a plurality of scent cartridges, each of the plurality of scent cartridges having an air inlet and an air outlet,
a member movably associated with the housing, the member having a first opening, the member configured to be moved relative to the housing to selectively align the first opening with the air inlet of at least a selected one of the plurality of the scent cartridges;
a fan configured to move air through the air inlet and the air outlet of the selected one of the plurality of scent cartridges; and
a motor coupled to the member and configured to move the member relative to the housing.

2. The fragrance dispenser of claim 1, wherein the member comprises an insert having a top portion, a bottom portion, and at least one side portion, the insert including a passageway extending between an entrance at the top portion and an exit at the side portion, the exit configured to be aligned with air inlet of the selected one of the plurality of the scent cartridges, and
wherein the housing comprises a plurality of second openings, each of the plurality of second openings configured to be aligned with the air outlet of one of the plurality of scent cartridges.

3. The fragrance dispenser of claim 1, wherein the member comprises an outer shell having a third opening, the third opening configured to be selectively aligned with the air outlet of one of the plurality of scent cartridges.

4. The fragrance dispenser of claim 1, further including a microcontroller programmed to control at least one of the fan and the motor.

5. The fragrance dispenser of claim 4, wherein the microcontroller is programmed to move the member back and forth between at least two positions at a predetermined frequency, the first position of the member enabling release of scent from a first one of the plurality of scent cartridges and the second position of the member enabling release of scent from a second one of the plurality of scent cartridges.

6. The fragrance dispenser of claim 4, wherein the microcontroller is programmed to vary a speed of the fan.

7. A fragrance emission device, comprising:
a base including a plurality of ducts, each of the plurality of ducts extending from an end portion of the base to a side portion of the base;
a plurality of inlet openings at the end portion of the base, each of the plurality of inlet openings being in communication with one of the plurality of ducts;
a plurality of outlet openings at the side portion of the base, each of the plurality of outlet openings being in communication with one of the plurality of ducts;
a fan positioned at the end portion of the base adjacent the plurality of inlet openings;
a motor in communication with the fan and adapted to actuate the fan;
a plurality of fragrance cartridges, each of the plurality of fragrance cartridges positionable to at least partially align with one of the plurality of outlet openings; and
a cover adapted to fit over the base, the cover including a release opening, configured to align the release opening with one of the plurality of outlet openings.

8. The device of claim 7, wherein the base and the covering are cylindrical;
and wherein the covering is rotatable relative to the base so as to align the release opening to at least one of the plurality of outlets.

9. The device of claim 7, wherein the base and the covering are spherical.

10. The device of claim 7, wherein the fragrance cartridges are configured to individually engage with the base.

11. The device of claim 10, wherein:
the base includes at least one receptacle extending parallel to the side portion along a vertical axis of the device; and
at least one of the plurality of fragrance cartridges is receivable within the at least one receptacle.

12. The device of claim 10, wherein the fragrance cartridges are adapted to attach to an outer surface of the base.

13. The device of claim 10, wherein each fragrance cartridge comprises a reservoir at an upper portion thereof and a porous material positioned between the reservoir and an exterior of the fragrance cartridge at a lower portion.

14. The device of claim 7, wherein the motor is configured to rotate at least one of the base and the covering to adjust an alignment between the release opening of the cover and the plurality of outlet openings.

15. The device of claim 14, further comprising a microcontroller programmed to control operation of the motor.

16. The device of claim 15, wherein the microcontroller is programmed to vary a speed of the fan.

17. The device of claim 7, wherein each of the plurality of ducts extends at least partially along a radius of curvature.

18. The device of claim 7, wherein the release opening comprises multiple release openings, and
wherein the covering comprises a plurality of covering elements, each of the plurality of covering elements associated with one of the release openings, each of the plurality of covering elements configured to selectively cover and uncover the associated release opening.

19. A system for emitting a variety of fragrances, comprising:
a base including a passageway extending from an end portion of the base to a side portion of the base and having an inlet opening at the end portion;
a plurality of outlet openings at the side portion of the base, each of the plurality of outlet openings being in communication with the passageway;
a fan positioned at the end portion of the base adjacent the inlet opening;
a motor in communication with the fan and adapted to actuate the fan;
a plurality of fragrance cartridges, each of the plurality of fragrance cartridges positionable to at least partially align with the plurality of outlet openings; and
a cover adapted to fit over the base, the cover including a release opening, and being rotatable with respect to the base, such that the release opening aligns with one of the plurality of outlet openings.

* * * * *